(12) United States Patent
Gorospe

(10) Patent No.: US 7,699,862 B2
(45) Date of Patent: *Apr. 20, 2010

(54) RESHEATHING TOOL

(75) Inventor: Marcelino Gorospe, Redwood City, CA (US)

(73) Assignee: Micrus Corporation, San Jose, CA (US)

( * ) Notice: Subject to any disclaimer, the term of this patent is extended or adjusted under 35 U.S.C. 154(b) by 1041 days.

This patent is subject to a terminal disclaimer.

(21) Appl. No.: 11/043,032

(22) Filed: Jan. 25, 2005

(65) Prior Publication Data

US 2006/0167488 A1 Jul. 27, 2006

(51) Int. Cl.
 *A61M 29/00* (2006.01)
(52) U.S. Cl. ....................................... 606/191
(58) Field of Classification Search ................. 606/191, 606/194, 200
 See application file for complete search history.

(56) References Cited

U.S. PATENT DOCUMENTS

| 3,459,184 A | | 8/1969 | Ring | |
|---|---|---|---|---|
| 3,815,604 A | * | 6/1974 | O'Malley et al. | 604/22 |
| 4,887,997 A | * | 12/1989 | Okada | 604/516 |
| 5,350,397 A | * | 9/1994 | Palermo et al. | 606/200 |
| 5,380,290 A | * | 1/1995 | Makower et al. | 604/164.01 |
| 5,507,769 A | | 4/1996 | Marin et al. | |
| 5,527,336 A | | 6/1996 | Rosenbluth et al. | |
| 5,743,875 A | * | 4/1998 | Sirhan et al. | 604/96.01 |
| 5,755,685 A | | 5/1998 | Andersen | |
| 5,863,294 A | * | 1/1999 | Alden | 606/167 |
| 6,273,899 B1 | * | 8/2001 | Kramer | 606/194 |
| 6,299,595 B1 | * | 10/2001 | Dutta et al. | 604/96.01 |
| 6,447,540 B1 | * | 9/2002 | Fontaine et al. | 623/1.12 |
| 7,018,394 B2 | * | 3/2006 | Diaz et al. | 606/200 |
| 2003/0093085 A1 | * | 5/2003 | Leopold et al. | 606/108 |

* cited by examiner

*Primary Examiner*—Kevin T Truong
(74) *Attorney, Agent, or Firm*—Fulwider Patton LLP

(57) ABSTRACT

The resheathing tool includes a flexible tubular body with a wall, an inner bore, and an aperture formed in the wall. The tool can be used to facilitate the unsheathing of the vasoocclusive device from the reloadable slotted introducer sheath by threading a proximal portion of the sheath out the aperture of the tool while sliding the vasoocclusive device distally through the sheath. The tool facilitates resheathing of the vasoocclusive device by introducing the vasoocclusive device through the slot of a reloadable slotted introducer sheath into the sheath by threading the reloadable slotted introducer sheath through the aperture and into the inner bore of the tool while threading the vasoocclusive device through the inner bore of the tool. At the same time, the resheathing tool prevents the elongated vasoocclusive device from moving out of the reloadable slotted introducer sheath through the slot.

7 Claims, 3 Drawing Sheets

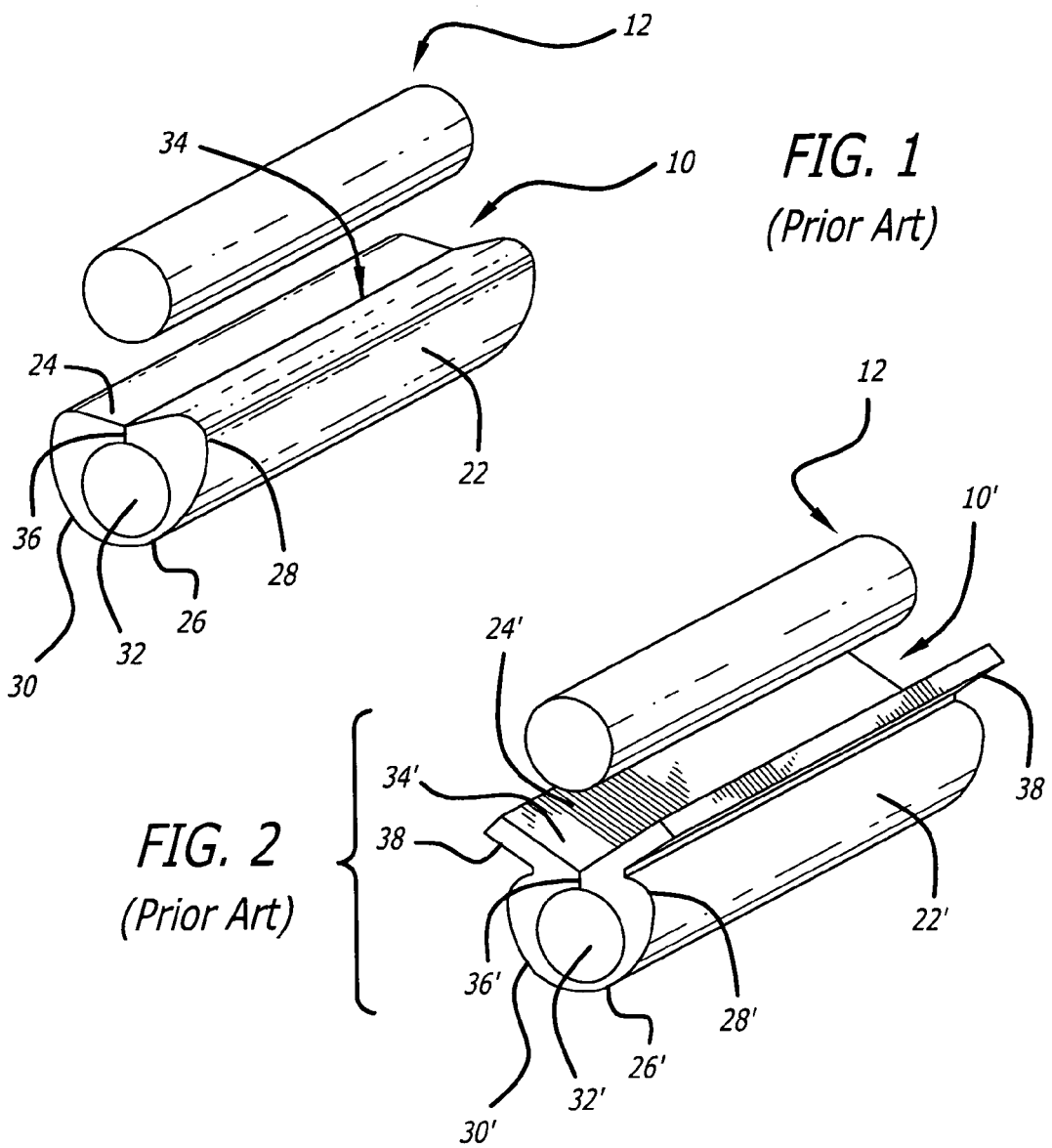
FIG. 1 (Prior Art)
FIG. 2 (Prior Art)
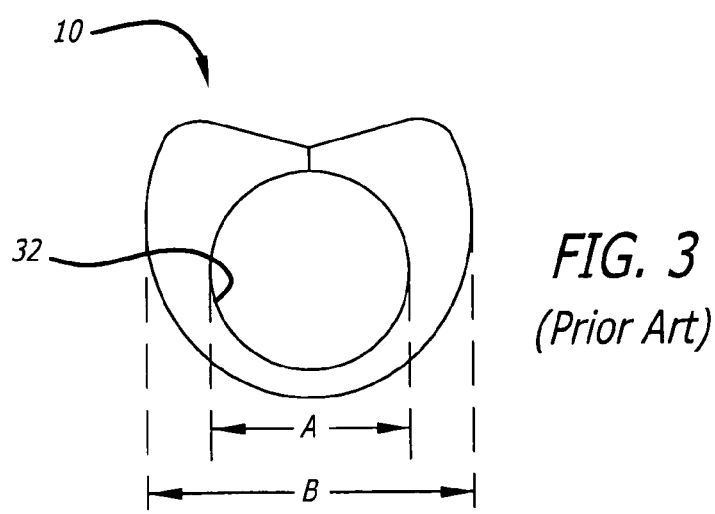
FIG. 3 (Prior Art)

RESHEATHING TOOL

BACKGROUND OF THE INVENTION

1. Field of the Invention

This invention relates generally to devices for interventional therapeutic treatment or vascular surgery for treatment of defects in the vasculature, and more particularly concerns a system and method for delivering intravascular interventional devices, such as for treatment of aneurysms.

2. General Background and State of the Art

Vascular interventional devices such as vasoocclusive devices are typically placed within the vasculature of the human body by use of a catheter. Vascular interventional devices such as stents can be placed within an occluded vessel to facilitate blood flow through the vessel, and vasoocclusive devices are typically either placed within a blood vessel to block the flow of blood through a vessel making up that portion of the vasculature by the formation of an embolus, or are placed within an aneurysm stemming from the vessel to form such an embolus within the aneurysm. Vasoocclusive devices used for these procedures can have a wide variety of configurations, and aneurysms have been treated with external surgically placed clips, detachable vasoocclusive balloons and embolus generating vasoocclusive devices such as one or more vasoocclusive or embolic coils.

The delivery of such vasoocclusive devices has typically been accomplished by a variety of means, including via a catheter in which the device is pushed through an opening at the distal end of the catheter by an elongated flexible pusher member to deploy the device. The vasoocclusive devices can be produced in such a way that they will pass through the lumen of a catheter in a linear shape and take on a complex shape as originally formed after being deployed into the area of interest, such as in an aneurysm.

Detachable vasoocclusive devices are typically embolic coils fixed to a distal end of a flexible pusher member for delivery of the embolic coils, and may be detached mechanically, electrically or by some other means from the flexible pusher member at the target location. The detachable embolic coils can be delivered to the target location and detached if correctly sized and positioned, or the embolic coils may be withdrawn without being detached if the coils are not correctly sized, if the coils are not correctly positioned, or if the microcatheter positioning is lost. Some available vasoocclusive devices are not reused during a patient procedure if they are removed during the procedure, due to the inability to reload the device into the microcatheter. It is therefore desirable to provide a system and method for reusing vasoocclusive devices during a clinical procedure after removal from a microcatheter introducer.

One such system and method allowing the reuse of vasoocclusive devices after removal from a microcatheter introducer during a clinical procedure provides for an introducer sheath for a therapeutic vasoocclusive device which includes an assembly of a flexible pusher member and an embolic coil. The introducer sheath is formed from a hollow, elongated tubular member, and includes a longitudinal slot formed in the upper wall of the introducer sheath and extending the length, or majority of the length, of elongated tubular member. The slot permits introduction of the vasoocclusive device into the interior channel of the introducer sheath, and permits the introducer sheath to release the vasoocclusive device for introduction into a microcatheter, for deployment during a clinical procedure. The vasoocclusive device can be manually placed into the introducer sheath by an operator by using the finger and thumb of one hand to pinch the device positioning unit into the introducer sheath. Similarly, the vasoocclusive device can be manually released from the introducer sheath by pinching the introducer sheath to open the slot, and bending the introducer sheath to expose the distal tip of the vasoocclusive device, which can then be stripped out of the introducer sheath along the length of the slot. However, such manual techniques of sheathing and unsheathing a vasoocclusive device from the introducer sheath are highly dependent upon the manual dexterity of the operator. It would be desirable to improve the resheathing and unsheathing of a vasoocclusive device from such an introducer sheath by providing a tool that will aid in the unsheathing and resheathing of the vasoocclusive device in such an introducer sheath. The present invention satisfies these and other needs.

INVENTION SUMMARY

Briefly, and in general terms, the invention provides for a tool to facilitate the unsheathing and resheathing of a vasoocclusive device, which includes a flexible pusher member and an embolic coil, in a reloadable slotted introducer sheath. The resheathing tool is formed from a round tube that slides over the reloadable slotted introducer sheath. The tubular resheathing tool advantageously includes an aperture approximately at the middle of the tubular resheathing tool which aids in the unsheathing of the vasoocclusive device from the reloadable slotted introducer sheath during introduction of the vasoocclusive device into a microcatheter for deployment of the vasoocclusive device in treatment of a patient, and which aids in the resheathing of the vasoocclusive device in the reloadable slotted introducer sheath. The tubular resheathing tool also provides a mechanism for locking the reloadable slotted introducer sheath and vasoocclusive device together.

The present invention accordingly provides for a resheathing tool having a flexible tubular body with a wall, a central inner bore, proximal and distal ends, and an aperture formed in the wall of the flexible tubular body approximately midway between the proximal and distal ends of the flexible tubular body. In a presently preferred aspect, the aperture is formed as a slanted notch shaped aperture in one side of the flexible tubular body with a first slanted edge at a proximal end of the slanted notch shaped aperture extending from the exterior surface of the flexible tubular member distally, and inwardly to about half of the diameter of the flexible tubular member, and with a second transverse edge at a distal end of the slanted notch shaped aperture extending approximately perpendicular to the axis of the flexible tubular member, from the exterior surface to meet the distal end of the slanted edge. The slanted notch shaped aperture provides an oblique ramp on the slanted edge extending from the inner surface of the wall of the flexible tubular member to the outer surface of the wall of the flexible tubular member.

In the method of the invention, the tool can be used for progressively unsheathing an elongated vasoocclusive device from a reloadable slotted introducer sheath by threading the reloadable slotted introducer sheath out through the aperture of the tool, while threading the elongated vasoocclusive device distally toward a patient through the inner bore of the reloadable slotted introducer sheath, and sliding the resheathing tool distally toward the patient over the reloadable slotted introducer sheath, to deliver the elongated vasoocclusive device through a delivery catheter to a desired treatment target site in the vasculature of the patient.

The tool can also be used to facilitate the resheathing of the elongated vasoocclusive device in the reloadable slotted introducer sheath, by advancing the tool proximally away from the patient over the reloadable slotted introducer sheath, which is received in the inner bore of the tool through the aperture of the tool, and over the elongated vasoocclusive device which is received in the inner bore of the tool and pressed through the slot of the reloadable slotted introducer sheath into the inner bore of the reloadable slotted introducer sheath.

Other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

FIG. 1 is a perspective view of a first embodiment of a prior art reloadable slotted introducer sheath for a vasoocclusive device.

FIG. 2 is a perspective view of a second embodiment of a prior art reloadable slotted introducer sheath for a vasoocclusive device.

FIG. 3 is a cross-sectional view of the prior art reloadable slotted introducer sheath of FIG. 1.

DETAILED DESCRIPTION OF THE PREFERRED EMBODIMENTS

Figure 4:
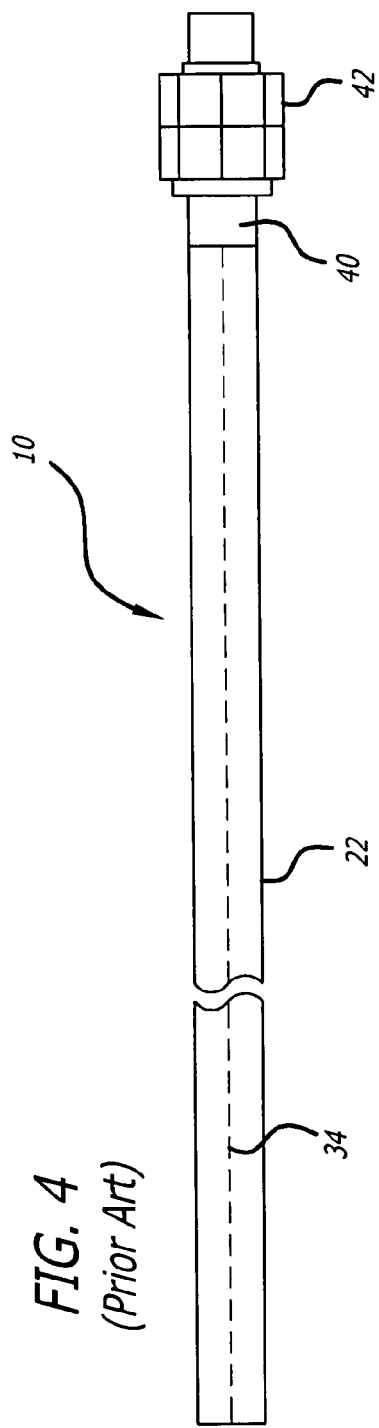
FIG. 4 is a schematic diagram of the prior art reloadable slotted introducer sheath to be used with the resheathing tool according to the invention.
Figure 5:
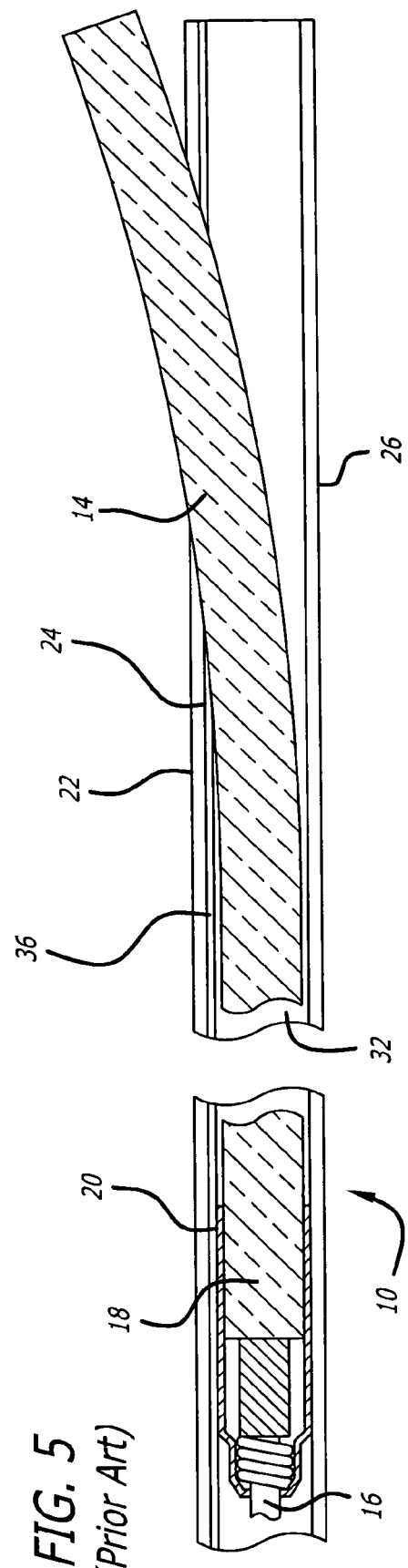
FIG. 5 is a longitudinal sectional view of the prior art reloadable slotted introducer sheath in combination with a vasoocclusive device, showing the advancing of the vasoocclusive device through the reloadable slotted introducer sheath.

Referring to the drawings, which are provided for purposes of illustration and by way of example, one example of a prior art reloadable slotted introducer sheath 10 for a therapeutic vasoocclusive device 12 is illustrated in FIGS. 1-5. The vasoocclusive device typically includes an assembly of an elongated flexible pusher member 14 and an embolic coil 16 (only a portion of which is shown) attached to the flexible pusher member, as illustrated in FIGS. 4 and 5. The elongated flexible pusher member may, for example, include an elongated optical fiber having a distal end 18 sheathed in a tubular collar 20 of shape memory material for retaining the embolic coil on the distal end of the flexible pusher member. The optical fiber can be sized to be quite flexible and bend sufficiently to follow the body lumen. Alternatively, the elongated flexible pusher member can be formed of suitable materials for conducting energy, such as radio frequency energy, magnetic energy, electrical energy, or ultrasonic energy, such as an elongated metal member, for example, or of a heat pipe for conducting heat from a heat source. Alternatively, the flexible pusher can consist of a tubular or solid wire construction with attachment to an embolic coil to allow, for example, deployment by mechanical or hydraulic means.

Referring to FIGS. 1 and 3-5, the reloadable slotted introducer sheath is generally formed of a hollow, elongated tubular member 22 having an upper wall 24 and an opposing lower wall 26, opposing side walls 28 and 30, and a longitudinal interior channel 32. The upper wall of the elongated tubular member includes a slot 34 or slit with opposing interior sides 36 having surfaces extending through the upper wall leading to the interior channel, permitting introduction of the vasoocclusive device into the interior channel. The reloadable slotted introducer sheath may have the exemplary dimensions illustrated in FIGS. 3 and set forth in the table below. In the table, "A" indicates a possible longitudinal interior channel dimension (32) and "B" indicates a possible outer diameter sheath dimension.

| System | "A" (in.) | "B" (in.) |
| --- | --- | --- |
| 10 | 0.016 | 0.030 |
| 18 | 0.020 | 0.034 |

As is best seen in FIGS. 1 and 3 the upper wall of the elongated tubular member adjacent to the slot typically has an outer angled or V-shaped configuration on the outside surface of the tubing, to facilitate loading of the vasoocclusive device into the reloadable slotted introducer sheath. The slot may, for example, have opposing exterior surfaces forming an interior angle of about 110° to 150°. The lower wall of the tubing is typically about 0.002 to 0.004 inches thick to allow opposing sides of the slot of the hollow, elongated tubular member to flex outwardly to allow the slot to open to accept the vasoocclusive device. The configuration allows the flexible pusher member to be inserted into the reloadable slotted introducer sheath by positioning the flexible pusher member and embolic coil assembly over the slot and providing a sliding pressure, such as by a person's thumb, along the length of the flexible pusher member and embolic coil assembly to introduce the flexible pusher member and embolic coil assembly into the sheath. In this embodiment, the sheath is fully removable from the flexible pusher member.

FIG. 2 illustrates a second embodiment of a prior art reloadable slotted introducer sheath 10' for a therapeutic vasoocclusive device 12, which typically includes an assembly of a flexible pusher member 14 and an embolic coil 16, described above and illustrated in FIGS. 4 and 5. The reloadable slotted introducer sheath 10' is generally formed of a hollow, elongated tubular member 22' having an upper wall 24' and an opposing lower wall 26', opposing side walls 28' and 30', and a longitudinal interior channel 32'. The upper wall of the elongated tubular member includes a slot 34' with opposing interior sides 36' having surfaces extending through the upper wall leading to the interior channel, permitting introduction of the vasoocclusive device into the interior channel.

The upper wall of the elongated tubular member adjacent to the slot typically has an outer angled or V-shaped configuration on the outside surface of the tubing, to facilitate loading of the vasoocclusive device into the reloadable slotted introducer sheath. The slot may, for example, have opposing exterior surfaces forming an interior angle of about 110° to 150°. The lower wall of the tubing is typically about 0.002 to 0.004 inches thick to allow opposing sides of the slot of the hollow, elongated tubular member to flex outwardly to allow the slot to open to accept the vasoocclusive device. In this embodiment, the upper angled surface portions of the upper wall of the elongated tubular member adjacent to the slot may be formed as outwardly extending walls or wing members 38 to facilitate insertion of the flexible pusher member and embolic coil assembly into the slotted sheath.

As is illustrated in FIGS. 4 and 5, a reloadable slotted introducer sheath according to the invention receives an elongated vasoocclusive device that includes an assembly of the flexible pusher member 14 and an embolic coil 16, and that is adapted to be inserted into a portion of a patient's vasculature for occluding a portion of the vasculature for use in interventional therapy and vascular surgery. An unslotted segment 40 of the reloadable slotted introducer sheath remains unslotted, such as a segment of length less than the unused working length of the pusher when fully loaded into the microcatheter, for example, about 10 cm., so that the sheath can be pulled off of the vasoocclusive device along the slot as the vasoocclusive device is threaded through a delivery catheter for placement of the embolic coil in the vasculature of the patient, until the segment of the reloadable slotted introducer sheath without a slot is reached. The unslotted segment of the reloadable slotted introducer sheath is typically received in a rotating hemostatic valve 42, which clamps the reloadable slotted introducer sheath, while allowing the elongated vasoocclusive device to slide through the sheath. The portion of the reloadable slotted introducer sheath threaded out through the aperture of the tool can be looped and left attached to the end of the flexible pusher member while the flexible pusher member is loaded into a microcatheter (not shown). If the elongated vasoocclusive device is removed without detachment and placement of the embolic coil, the sheath can be loaded back onto the flexible pusher member starting at the connected location by reversing the process and progressing toward an end of the flexible pusher member away from the patient. The sheath can be advanced in this manner to cover substantially the entire elongated vasoocclusive device to allow the vasoocclusive device to be advanced into a microcatheter at a later time.

Figure 6:
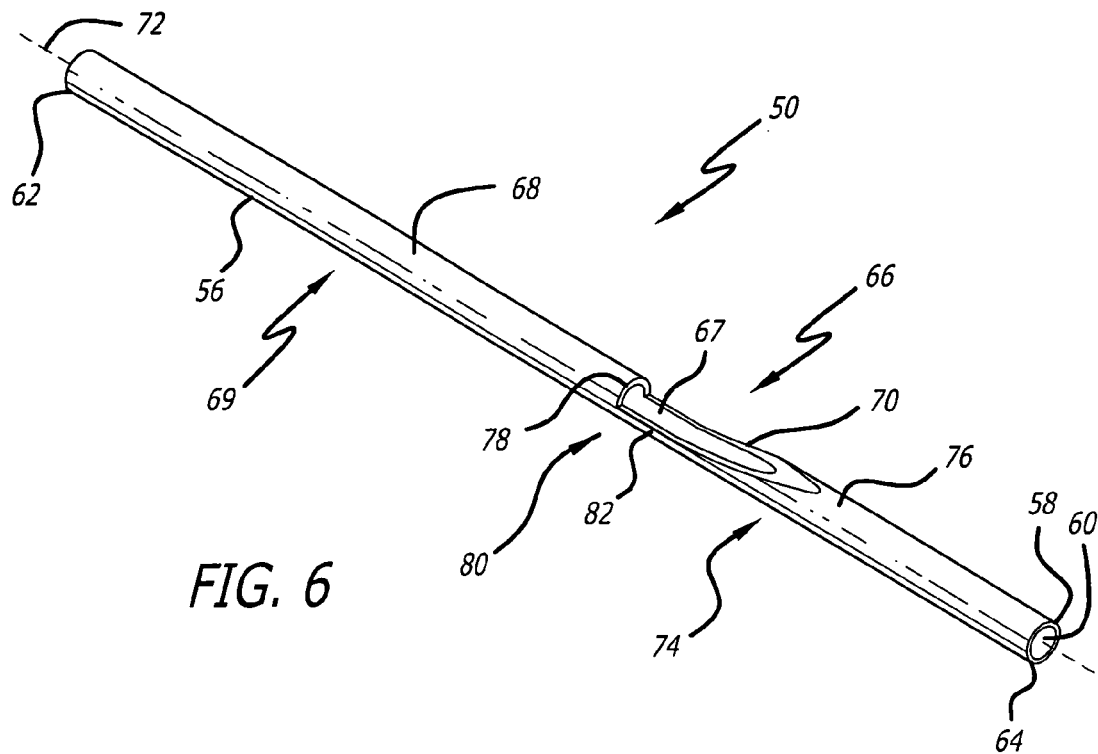
FIG. 6 is a perspective view of the resheathing tool of the present invention.
Figure 7:
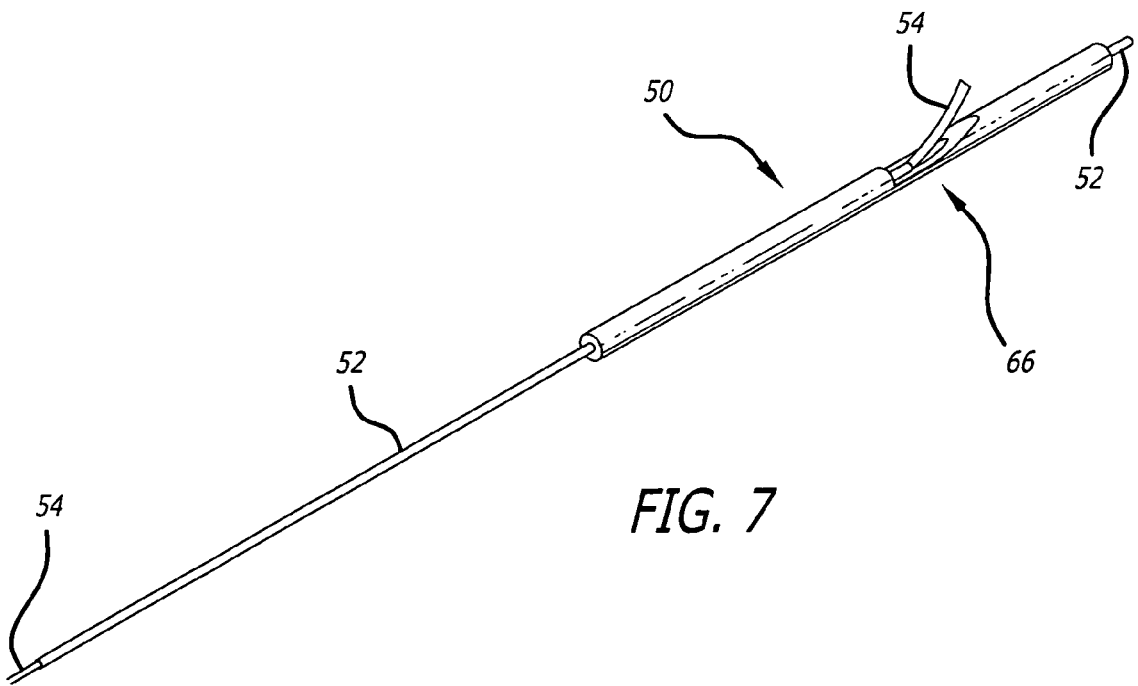
FIG. 7 is a diagram of the resheathing tool of FIG. 6 showing the disposition of a reloadable slotted introducer sheath and vasoocclusive device in the resheathing tool for purposes of unsheathing or resheathing the vasoocclusive device according to the present invention.

Referring to FIGS. 6 and 7, the present invention provides for a resheathing tool 50 to facilitate the unsheathing and resheathing of the combination of a reloadable slotted introducer sheath 52 (shown in FIG. 7), such as described above, and a vasoocclusive device 54 to be disposed in the reloadable slotted introducer sheath. As described above, the vasoocclusive device typically includes a flexible pusher member and an embolic coil. The resheathing tool is typically formed from a round tube, and includes a flexible tubular body 56 with a wall 58 and a central inner bore 60 that slides over the reloadable slotted introducer sheath, a distal end 62 and a proximal end 64. The tubular resheathing tool advantageously includes an aperture 66 with an opening 67 formed in the wall of the flexible tubular body approximately midway between the proximal and distal ends of the flexible tubular body to aid in the unsheathing of the vasoocclusive device from the reloadable slotted introducer sheath during introduction of the vasoocclusive device into a microcatheter for deployment of the vasoocclusive device in treatment of a patient, and sheathing or resheathing of the vasoocclusive device in the reloadable slotted introducer sheath, as will be further explained below. When the reloadable slotted introducer sheath and vasoocclusive device pass through the distal portion 69 of the resheathing tool, the tubular resheathing tool also serves to lock the reloadable slotted introducer sheath and vasoocclusive device together.

In a presently preferred aspect, the aperture is formed as a slanted notch shaped aperture in one side 68 of the flexible tubular body with a first, slanted edge 70 that is slanted or oblique with respect to the longitudinal axis 72 of the flexible tubular body at a proximal end 74 of the slanted notch shaped aperture extending from the exterior surface 76 of the flexible tubular member distally and inwardly to about half or slightly more of the diameter of the flexible tubular member, and with a second, transverse edge 78 that is approximately perpendicular to the longitudinal axis of the flexible tubular body at a distal end 80 of the slanted notch shaped aperture, extending from the exterior surface of the flexible tubular body to meet the distal end 82 of the slanted edge. The slanted notch shaped aperture provides an oblique ramp on the slanted edge.

As is illustrated in FIG. 7, in the method of the invention, the resheathing tool can be used in combination with a reloadable slotted introducer sheath 52 and an elongated vasoocclusive device 54 to progressively unsheathe and advance the elongated vasoocclusive device through the inner bore of the resheathing tool and through the central bore of the reloadable slotted introducer sheath by threading the reloadable slotted introducer sheath out through the aperture of the tool, and sliding the elongated vasoocclusive device through the inner bore of the reloadable slotted introducer sheath. While the resheathing tool slides distally toward the patient over the reloadable slotted introducer sheath, the elongated vasoocclusive device can be pushed distally toward the patient and slide through the reloadable slotted introducer sheath even as the reloadable slotted introducer sheath is clamped by a rotating hemostatic valve, to be delivered to a target site in the vasculature of the patient.

Similarly, the resheathing tool can be used in combination with a reloadable slotted introducer sheath and an elongated vasoocclusive device to facilitate the resheathing of the vasoocclusive device in the reloadable slotted introducer sheath. Again referring to FIG. 7, to sheathe the vasoocclusive device in the reloadable slotted introducer sheath, the elongated vasoocclusive device is introduced and advanced into the inner bore of the flexible tubular body of the tool at a proximal end of the flexible tubular body of the tool as the tool slides proximally along the reloadable slotted introducer sheath and elongated vasoocclusive device away from the patient, and the reloadable slotted introducer sheath is advanced into the inner bore of the flexible tubular body of the tool through the aperture of the tool, to press the vasoocclusive device through the longitudinal slot of the reloadable slotted introducer sheath into the inner bore of the reloadable slotted introducer sheath. At the same time, the disposition of the reloadable slotted introducer sheath in the resheathing tool prevents the elongated vasoocclusive device from moving out of the reloadable slotted introducer sheath through the slot, locking the elongated vasoocclusive device in the reloadable slotted introducer sheath.

In each of the foregoing embodiments, the elongated tubular member forming the reloadable slotted introducer sheath is typically formed from a thermoplastic material. The tubing may be formed from a thermoplastic material such as high density polyethylene, for example. Alternatively, other similar polymeric materials may also be suitable, such as polyurethane, nylons, polyetheretherketone (PEEK), polytetrafluoroethylene (PTFE), polyethylene terephthalate (PET), and the like.

It will be apparent from the foregoing that, while particular forms of the invention have been illustrated and described, various modifications can be made without departing from the spirit and scope of the invention. Accordingly, it is not intended that the invention be limited, except as by the appended claims.

The invention claimed is:

1. A tool to facilitate the unsheathing of a vasoocclusive device from a reloadable slotted introducer sheath adapted to receive the vasoocclusive device, and to facilitate the resheathing of the vasoocclusive device in the reloadable slotted introducer sheath, the vasoocclusive device including an elongated flexible pusher member and an embolic coil connected to the elongated flexible pusher member, the tool comprising:

a flexible tubular body including a wall, an inner bore, a proximal end and a distal end, the inner bore being adapted to slide over and receive the reloadable slotted introducer sheath and the vasoocclusive device; and an aperture formed in the wall of the flexible tubular body to aid in the unsheathing of the vasoocclusive device from the reloadable slotted introducer sheath for deployment of the vasoocclusive device in treatment of a patient, and to aid in resheathing of the vasoocclusive device into the reloadable slotted introducer sheath, wherein said aperture is formed approximately midway between the proximal and distal ends of the flexible tubular body in one side of the flexible tubular body with a first, slanted edge that is slanted with respect to a longitudinal axis of the flexible tubular body extending from a proximal end of the aperture at the exterior surface of the flexible tubular member distally and inwardly to a distal end of the aperture at about half of the diameter of the flexible tubular member, and with a second, transverse edge that is approximately perpendicular to the longitudinal axis of the flexible tubular body at the distal end of the aperture, extending from the exterior surface of the flexible tubular body to meet the slanted edge at the distal end of the aperture.

2. The tool of claim 1, wherein said slanted edge provides an oblique ramp for the reloadable slotted introducer sheath.

3. A tool to facilitate the unsheathing of a vasoocclusive device from a reloadable slotted introducer sheath adapted to receive the vasoocclusive device, and to facilitate the resheathing of the vasoocclusive device in the reloadable slotted introducer sheath, the vasoocclusive device including an elongated flexible pusher member and an embolic coil connected to the elongated flexible pusher member, the tool comprising:

a flexible tubular body including a wall, an inner bore, a proximal end and a distal end, the inner bore being adapted to slide over and receive the reloadable slotted introducer sheath and the vasoocclusive device; and a slanted notch shaped aperture formed in the wall of the flexible tubular body to aid in the unsheathing of the vasoocclusive device from the reloadable slotted introducer sheath for deployment of the vasoocclusive device in treatment of a patient, and to aid in resheathing of the vasoocclusive device into the reloadable slotted introducer sheath, wherein said slanted notch shaped aperture is formed approximately midway between the proximal and distal ends of the flexible tubular body in one side of the flexible tubular body with a first, slanted edge that is slanted with respect to a longitudinal axis of the flexible tubular body extending from a proximal end of the slanted notch shaped aperture at the exterior surface of the flexible tubular member distally and inwardly to a distal end of the slanted notch shaped aperture at about half of the diameter of the flexible tubular member, and with a second, transverse edge that is approximately perpendicular to the longitudinal axis of the flexible tubular body at the distal end of the slanted notch shaped aperture, extending from the exterior surface of the flexible tubular body to meet the slanted edge at the distal end of the slanted notch shaped aperture.

4. The tool of claim 3, wherein said slanted edge provides an oblique ramp for the reloadable slotted introducer sheath.

5. A method for facilitating the sheathing of a vasoocclusive device in a reloadable slotted introducer sheath having a longitudinal slot and an inner channel, the vasoocclusive device having a proximal end and a distal end and including an elongated flexible pusher member and an embolic coil connected to the elongated flexible pusher member, the method comprising:

providing a tool including a flexible tubular body having a wall with an aperture formed in the wall, an inner bore, a proximal end and a distal end, the inner bore of the tool being adapted to slide over and receive the reloadable slotted introducer sheath and the vasoocclusive device, wherein said aperture is formed approximately midway between the proximal and distal ends of the flexible tubular body in one side of the flexible tubular body with a first, slanted edge that is slanted with respect to a longitudinal axis of the flexible tubular body extending from a proximal end of the aperture at the exterior surface of the flexible tubular member distally and inwardly to a distal end of the aperture at about half of the diameter of the flexible tubular member, and with a second, transverse edge that is approximately perpendicular to the longitudinal axis of the flexible tubular body at the distal end of the aperture, extending from the exterior surface of the flexible tubular body to meet the slanted edge at the distal end of the aperture;

introducing a portion of the reloadable slotted introducer sheath through the aperture of the tool into the inner bore of the tool;

introducing a portion of the vasoocclusive device into the inner bore of the tool adjacent to the longitudinal slot of the reloadable slotted introducer sheath; and progressively sliding the reloadable slotted introducer sheath through the aperture into the inner bore of the tool and sliding the vasoocclusive device through the inner bore of the tool to press the vasoocclusive device through the longitudinal slot of the reloadable slotted introducer sheath into the inner channel of the reloadable slotted introducer sheath to thereby sheathe the vasoocclusive device in the reloadable slotted introducer sheath.

6. A method for facilitating the unsheathing of a vasooclusive device from a reloadable slotted introducer sheath having a longitudinal slot and an inner channel, the vasoocclusive device having a proximal end and a distal end and including an elongated flexible pusher member and an embolic coil connected to the elongated flexible pusher member, at least a portion of the vasoocclusive device being disposed within the reloadable slotted introducer sheath, the method comprising:

providing a tool including a flexible tubular body having a wall, an inner bore, a proximal end and a distal end, and an aperture formed in the wall, the inner bore of the flexible tubular body being adapted to slide over and receive the reloadable slotted introducer sheath and the vasoocclusive device, wherein said aperture is formed approximately midway between the proximal and distal ends of the flexible tubular body in one side of the flexible tubular body with a first, slanted edge that is slanted with respect to a longitudinal axis of the flexible tubular body extending from a proximal end of the aperture at the exterior surface of the flexible tubular member distally and inwardly to a distal end of the aperture at about half of the diameter of the flexible tubular member, and with a second, transverse edge that is approximately perpendicular to the longitudinal axis of the flexible tubular body at the distal end of the aperture, extending from the exterior surface of the flexible tubular body to meet the slanted edge at the distal end of the aperture;

introducing the reloadable slotted introducer sheath and vasoocclusive device with at least a portion of the vasoocclusive device disposed in the reloadable slotted introducer sheath into the inner bore of the flexible tubular body of the tool;

advancing a proximal portion of the reloadable slotted introducer sheath and vasoocclusive device through the inner bore of the flexible tubular body of the tool; and advancing the proximal portion of the reloadable slotted introducer sheath proximally out the aperture while simultaneously advancing the vasoocclusive device distally through the inner bore of the tool and through the inner channel of the reloadable slotted introducer sheath.

7. The method of claim 6, further comprising resheathing the vasoocelusive device in the reloadable slotted introducer sheath by the steps of:

introducing a portion of the reloadable slotted introducer sheath through the aperture of the tool into the inner bore of the tool;

introducing a portion of the vasoocclusive device into the inner bore of the tool adjacent to the longitudinal slot of the reloadable slotted introducer sheath; and progressively sliding the reloadable slotted introducer sheath through the aperture into the inner bore of the tool and sliding the vasoocclusive device through the inner bore of the tool to press the vasoocclusive device through the longitudinal slot of the reloadable slotted introducer sheath into the inner channel of the reloadable slotted introducer sheath to thereby sheathe the vasoocclusive device in the reloadable slotted introducer sheath.

* * * * *